(12) United States Patent
Gerber et al.

(10) Patent No.: US 8,812,117 B2
(45) Date of Patent: *Aug. 19, 2014

(54) THERAPY CONTROL USING RELATIVE MOTION BETWEEN SENSORS

(71) Applicant: Medtronic, Inc., Minneapolis, MN (US)

(72) Inventors: Martin T. Gerber, Maple Grove, MN (US); John C. Rondoni, Plymouth, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/907,567

(22) Filed: May 31, 2013

(65) Prior Publication Data

US 2013/0261698 A1    Oct. 3, 2013

Related U.S. Application Data

(63) Continuation of application No. 13/355,348, filed on Jan. 20, 2012, now Pat. No. 8,457,750, which is a continuation of application No. 11/800,654, filed on May 7, 2007, now Pat. No. 8,103,351.

(51) Int. Cl.
*A61N 1/365* (2006.01)
*A61N 1/36* (2006.01)

(52) U.S. Cl.
CPC ........ *A61N 1/36003* (2013.01); *A61N 1/36135* (2013.01)
USPC .......................................................... 607/48

(58) Field of Classification Search
USPC ........................................ 607/45, 46, 48, 117
See application file for complete search history.

(56) References Cited

U.S. PATENT DOCUMENTS

| 5,233,984 A | 8/1993 | Thompson |
| 5,342,409 A | 8/1994 | Mullett |
| 5,593,431 A | 1/1997 | Sheldon |

(Continued)

FOREIGN PATENT DOCUMENTS

| EP | 1195139 A1 | 4/2002 |
| WO | 03/065891 A2 | 8/2003 |
| WO | 2005/089860 | 9/2005 |

OTHER PUBLICATIONS

Notification of Transmittal of the International Search Report and the Written Opinion of the International Searching Authority, or the Declaration for corresponding PCT Application PCT/US2008/061098 dated Sep. 15, 2008 (16 pgs.).

(Continued)

*Primary Examiner* — Christopher D Koharski
*Assistant Examiner* — Jeremiah Kimball
(74) *Attorney, Agent, or Firm* — Shumaker & Sieffert, P.A.

(57) ABSTRACT

The invention is directed to controlling therapy delivery based on a relative motion between a first and second activity sensor. The relative motion between the activity sensors is representative of the relative motion between the locations of the body of the patient at which the respective activity sensors are located. The use of relative motion, however, may substantially remove motion experienced by both the activity sensors, e.g., motion caused by the environment in which patient is located, thus providing a new reference frame from which to analyze the motion measurements. The relative motion may be used to detect a condition of a movement disorder and/or control delivery of the therapy delivered to patient to treat or reduce the condition.

24 Claims, 4 Drawing Sheets

(56) References Cited

U.S. PATENT DOCUMENTS

| | | | |
|---|---|---|---|
| 5,851,193 A | 12/1998 | Arikka et al. | |
| 5,941,904 A | 8/1999 | Johnston et al. | |
| 6,044,297 A | 3/2000 | Sheldon et al. | |
| 6,449,508 B1 | 9/2002 | Sheldon et al. | |
| 6,659,968 B1 | 12/2003 | McClure | |
| 6,834,436 B2 | 12/2004 | Townsend et al. | |
| 7,110,820 B2 | 9/2006 | Tcheng et al. | |
| 7,130,681 B2 | 10/2006 | Gebhardt et al. | |
| 7,141,026 B2 | 11/2006 | Aminian et al. | |
| 7,151,961 B1 | 12/2006 | Whitehurst et al. | |
| 7,155,279 B2 | 12/2006 | Whitehurst et al. | |
| 7,167,743 B2 | 1/2007 | Heruth et al. | |
| 7,167,751 B1 | 1/2007 | Whitehurst et al. | |
| 7,313,440 B2 | 12/2007 | Miesel | |
| 7,330,760 B2 | 2/2008 | Heruth et al. | |
| 7,389,147 B2 | 6/2008 | Wahlstrand et al. | |
| 7,447,545 B2 | 11/2008 | Heruth et al. | |
| 7,519,431 B2 | 4/2009 | Goetz et al. | |
| 7,542,803 B2 | 6/2009 | Heruth et al. | |
| 7,769,464 B2 | 8/2010 | Gerber et al. | |
| 7,813,802 B2 | 10/2010 | Tcheng et al. | |
| 7,822,481 B2 | 10/2010 | Gerber et al. | |
| 7,853,322 B2 | 12/2010 | Bourget et al. | |
| 7,957,797 B2 | 6/2011 | Bourget et al. | |
| 7,957,809 B2 | 6/2011 | Bourget et al. | |
| 8,103,351 B2 * | 1/2012 | Gerber et al. | 607/48 |
| 8,457,750 B2 * | 6/2013 | Gerber et al. | 607/48 |
| 2002/0169485 A1 | 11/2002 | Pless et al. | |
| 2002/0170193 A1 | 11/2002 | Townsend et al. | |
| 2003/0149457 A1 | 8/2003 | Tcheng et al. | |
| 2004/0015103 A1 | 1/2004 | Aminian et al. | |
| 2004/0225332 A1 | 11/2004 | Gebhardt et al. | |
| 2005/0060001 A1 | 3/2005 | Singhal et al. | |
| 2005/0209645 A1 | 9/2005 | Heruth et al. | |
| 2005/0234514 A1 | 10/2005 | Heruth et al. | |
| 2006/0235289 A1 | 10/2006 | Wesselink et al. | |
| 2006/0247739 A1 | 11/2006 | Wahlstrand et al. | |
| 2006/0259099 A1 | 11/2006 | Goetz et al. | |
| 2007/0038265 A1 | 2/2007 | Tcheng et al. | |
| 2007/0073355 A1 | 3/2007 | Dilorenzo | |

OTHER PUBLICATIONS

Veltink et al., "Detection of Knee Instability Using Accelerometers—Experimental Test and Potential Use in the Control of FES—Assisted Paraplegic Standing," Engineering in Medincine and Biology Society, Proceedings of the 15th Annual International Conference of the IEEE Oct. 28-31, 1993, Piscataway, NJ, pp. 1232-1233.

Notification of Transmittal of the International Preliminary Report on Patentability dated Apr. 8, 2009 for corresponding PCT Application PCT/US2008/061098 (14 pgs.).

Reply to Written Opinion dated Mar. 5, 2009 for corresponding PCT Application PCT/US2008/061098 (15 pgs.).

Response dated Jun. 15, 2011 for European Examination Report for corresponding European Application No. 0876915.5, (6 pgs.).

European Examination Report dated Dec. 7, 2010 for corresponding European Application No. 08769151.5, (4 pgs.).

Prosecution History from U.S. Appl. No. 11/800,654, dated Mar. 9, 2009 through Sep. 16, 2011, 151 pp.

Prosecution History from U.S. Appl. No. 13/355,348, dated Oct. 10, 2012 through Feb. 12, 2013, 25 pp.

* cited by examiner

THERAPY CONTROL USING RELATIVE MOTION BETWEEN SENSORS

This application is a continuation of U.S. application Ser. No. 13/355,348, filed Jan. 20, 2012, which is a continuation of U.S. application Ser. No. 11/800,654, filed May 7, 2007 and issued as U.S. Pat. No. 8,103,351 on Jan. 24, 2012. The entire content of both applications is incorporated herein by reference.

TECHNICAL FIELD

The invention relates to medical devices and, more particularly, to medical devices that deliver therapy.

BACKGROUND

In some cases, an ailment results in problematic or symptomatic motion or activity by a patient. For example, any of a variety of movement disorders, such as tremor, epilepsy or Parkinson's disease, may have symptoms that result in irregular movement or activity. In the case of epilepsy, for example, the patient may experience recurring epileptic seizures, which may result in irregular movement or activity.

In some cases, a medical device may be used to deliver therapy to patients to treat these symptoms or conditions of the movement or other disorders. For example, an implantable neurostimulator may deliver electrical stimulation therapy to the patient to treat and/or reduce the symptoms of the movement disorders experienced by the patient. This may result in a decrease in symptomatic movement, or alleviation of an underlying cause of the symptomatic movement, e.g., termination of a seizure.

SUMMARY

In general, this disclosure describes techniques for using a relative motion between a first activity sensor and a second activity sensor to control delivery of a therapy to a patient. In particular, a therapy delivery device, or other device that controls the therapy delivery device, compares motion information measured by the first and second activity sensors to determine a relative motion between the activity sensors. In one embodiment, the first activity sensor may be located on or within the delivery device and the second activity sensor may be located on a limb of a patient.

The therapy delivery device may compare the magnitude and direction of the measured motions to compute the relative motion. The relative motion between the activity sensors is representative of the relative motion between the locations of the body of the patient at which the respective activity sensors are located. For example, in the case in which the first activity sensor is located in a delivery device implanted within the torso of the patient and the second activity sensor is located at a limb of the patient, the relative motion between the sensors is representative of the motion of the limb relative to motion of the torso of the patient. In this manner, the relative motion provides a new reference frame from which to analyze the motion measurements. In particular, the relative motion provides a reference frame in which motion experienced by both the activity sensors, e.g., motion caused by the environment in which patient is located, may be removed. The relative motion may be used to, for example, detect a condition of a movement disorder and/or control delivery of the therapy delivered to patient to treat or reduce the condition.

In one embodiment, a system comprises a therapy delivery device that delivers a therapy to a patient, a first activity sensor that generates a signal as a function of motion at a first location of a body of the patient, a second activity sensor that generates a signal as a function of motion at a second location of the body of the patient, and a processor that compares the signal generated by the first activity sensor and the signal generated by the second activity sensor to determine a relative motion of the second location of the patient relative to the first location of the patient. The processor further controls the therapy delivered to the patient based on the relative motion.

In another embodiment, a method comprises generating a signal as a function of motion at a first location of a body of a patient via a first activity sensor, generating a signal as a function of motion at a second location of the body of the patient via a second activity sensor, comparing the signal generated by the first activity sensor and the signal generated by the second activity sensor to determine a relative motion of the second location of the patient relative to the first location of the patient and controlling a therapy delivered to the patient based on the relative motion.

In another embodiment, a system comprises first means for generating a signal as a function of motion at a first location of a body of a patient via a first activity sensor, second means for generating a signal as a function of motion at a second location of the body of the patient via a second activity sensor, means for comparing the signal generated by the first generating means and the signal generated by the second generating means to determine a relative motion of the second location of the patient relative to the first location of the patient and means for controlling a therapy delivered to the patient based on the relative motion.

In another embodiment, a computer-readable medium contains instructions. The instructions cause a processor to generate a signal as a function of motion at a first location of a body of a patient via a first activity sensor, generate a signal as a function of motion at a second location of the body of the patient via a second activity sensor, compare the signal generated by the first activity sensor and the signal generated by the second activity sensor to determine a relative motion of the second location of the patient relative to the first location of the patient and control a therapy delivered to the patient based on the relative motion.

The details of one or more embodiments are set forth in the accompanying drawings and the description below. Other features, objects, and advantages will be apparent from the description and drawings, and from the claims.

DETAILED DESCRIPTION

Figure 1:
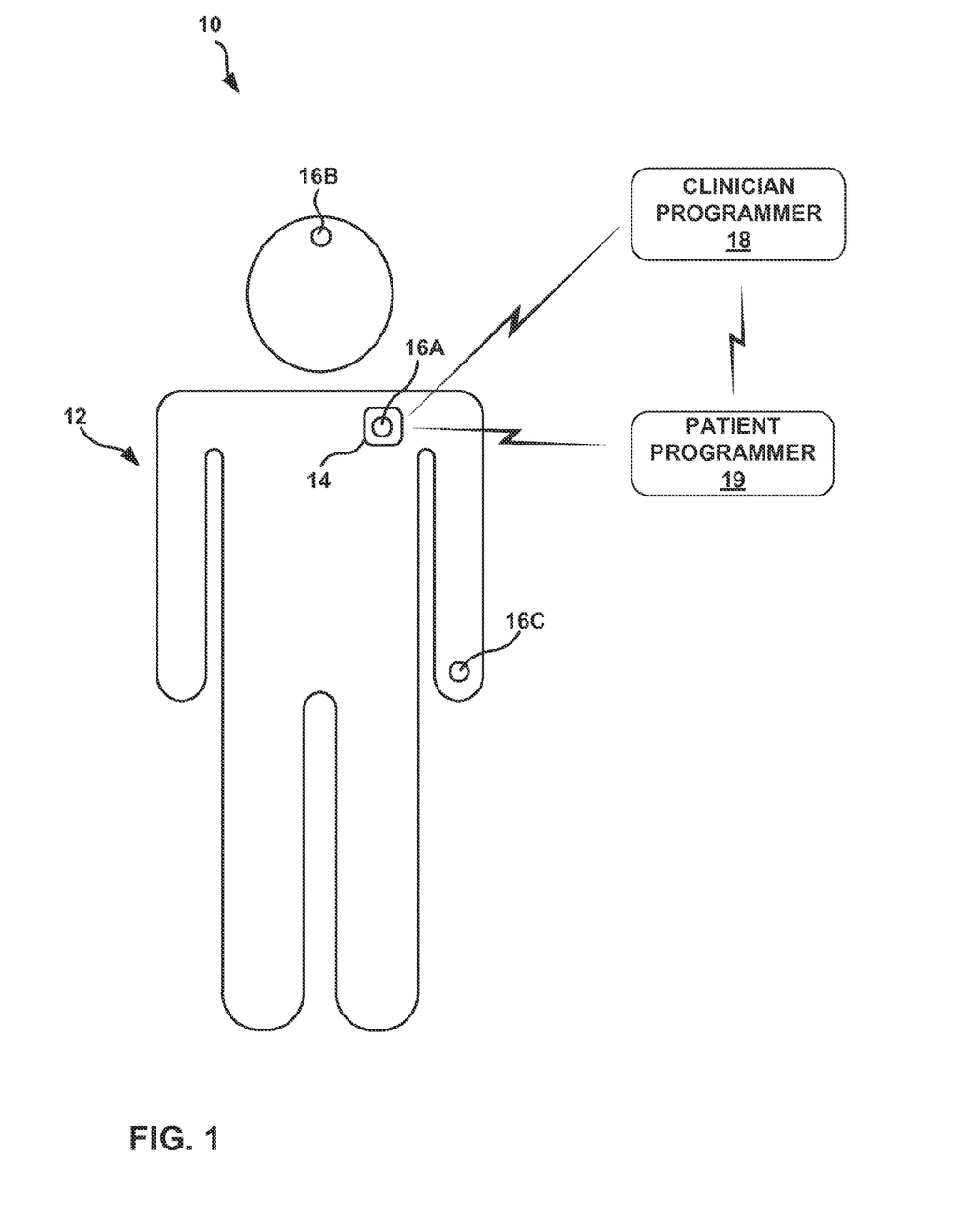
FIG. 1 is a conceptual diagram illustrating a system in conjunction with a patient 12.

FIG. 1 is a conceptual diagram illustrating a system 10 in conjunction with a patient 12. System 10 includes an implantable medical device (IMD) 14 that monitors and/or delivers a therapy to patient 12. IMD 14 may take the form of an implantable neurostimulator that delivers neurostimulation therapy in the form of one or more electrical pulses to patient 12 via one or more leads (not illustrated in FIG. 1). As one example, IMD 14 may take the form of an IMD that delivers deep brain stimulation (DBS) or cortical stimulation therapy to patient 12 to treat any of a variety of movement disorders. As used herein, the term "movement disorder" refers to a disorder that induces abnormal movement behavior of patient 12. Such disorders may include, but are not limited to tremor, Parkinson's disease, epilepsy, dystonia and the like. Alternatively, IMD 14 may be located elsewhere within patient 12, such as proximate to a spine of patient 12, proximate to a pelvis of patient 12 or the like. In this manner, IMD 14 may be used to provide therapy to target a variety of other disorders such as chronic pain, peripheral vascular disease, angina, headache, depression, urinary or fecal incontinence, sexual dysfunction, obesity, or gastroparesis.

IMD 14 delivers the therapy according to a set of therapy parameters, i.e., a set of values for a number of parameters that define the therapy delivered according to that therapy parameter set, which may also be referred to as a therapy program. In embodiments where IMD 14 delivers neurostimulation therapy in the form of electrical pulses, the parameters for each therapy parameter set may include voltage or current pulse amplitudes, pulse widths, pulse rates, duration, duty cycle and the like. Further, IMD 14 may be coupled to leads that include electrodes (not illustrated in FIG. 1), and each of the therapy parameter sets may include information identifying which electrodes have been selected for delivery of pulses, and the polarities of the selected electrodes. The information identifying selected electrodes and their polarities may be referred to as an electrode combination or configuration. In embodiments in which IMD 14 delivers other types of therapies, therapy parameter sets may include other therapy parameters such as drug concentration and drug flow rate in the case of drug delivery therapy. Therapy parameter sets used by IMD 14 may include a number of parameter sets programmed by a clinician (not shown), and parameter sets representing adjustments made by patient 12 or IMD 14 to these pre-programmed sets.

IMD 14 includes or is coupled to activity sensors 16A-16C (collectively, "activity sensors 16") that detect activity or motion of patient 12. In one embodiment, activity sensors 16 may comprise accelerometers that detect motions of patient 12. Activity sensors 16 may be multi-axis accelerometers or single-axis accelerometers. As illustrated in FIG. 1, activity sensors 16 may be located at different locations on patient 12. Activity sensor 16A may, for example, be located on or within a housing of IMD 14. Activity sensor 16B may be located on or within a lead that extends from IMD 14 into the brain of patient 12. Alternatively, activity sensor 16B may be a stand-alone sensor, i.e., not coupled to any lead, that is located externally or implanted within a head of patient 12. Activity sensor 16C is located at a limb of patient 12. In the example illustrated in FIG. 1, activity sensor 16C is located at an arm and, more particularly, at a wrist or hand of patient 12. Activity sensor 16C may, however, be located on a different limb of patient 12, such as on the other arm or on a leg. Activity sensors may be worn externally, e.g., on a piece of clothing or a watch, or implanted at the specific locations within patient 12. Although the example illustrated in FIG. 1 includes three activity sensors, system 10 may include more or less sensors, located at different locations on patient 12. The techniques of this disclosure may be utilized in any system that includes two or more activity sensors at different locations of patient 12.

Activity sensors 16 detect activity or motion at respective locations of patient 12. In particular, as patient 12 moves, activity sensors 16 detect the motion of the respective locations of the body of patient 12. Activity sensors 16 may, for example, generate signals as a function the motion of the respective portion of the body in terms of magnitude and direction. In the example illustrated in FIG. 1, activity sensor 16A detects motion of a torso of patient 12, activity sensor 16B detects motion of a head of patient 12 and activity sensor 16C detects motion of the limb of patient 12.

IMD 14 receives the signals from activity sensors 16. IMD 14 may receive the signals from at least a portion of activity sensors 16 via a wired connection. For example, IMD 14 may receive the signals from activity sensor 16A and 16B, if coupled to a lead, via a wired connection. Alternatively, IMD 14 may receive the signals from at least a portion of activity sensors 16 via wireless telemetry. For example, IMD 14 may receive a signal from activity sensor 16C via wireless telemetry. In this case, activity sensor 16C may include transmit circuitry to transmit the signals to IMD 14. Alternatively, one or more of activity sensors 16 may transmit the signals to a separate monitoring device, which relays the measurements to IMD 14.

IMD 14 may analyze the signals from activity sensors 16 instead of, or in addition to, other patient metrics measured by other sensors (not illustrated in FIG. 1) to detect one or more symptoms of a disorder, e.g., a movement disorder, for that IMD 14 is programmed to treat. Analyzing the signal of one of activity sensors 16 may provide information about basic body motion, but may not provide enough information in all cases. In fact, even analyzing the signals of multiple activity sensors 16 may not be sufficient. For example, IMD 14 may falsely identify onset of a seizure, tremor, or another symptom due to signals of one or more of activity sensors 16 when the patient is in an environment that causes awkward movements, such as a bumpy plane ride, automobile ride, or roller coaster ride, that may appear similar to a seizure or tremor.

Thus, IMD 14 compares signals of at least two of activity sensors 16 to determine a relative motion between activity sensors 16, and analyzes the relative motion between activity sensors 16 in accordance with the techniques of this disclosure. The relative motion represents the manner in which one location of patient 12 moves relative to another location of patient 12. Using relative motion, therefore, provides a different frame of reference, thus providing for more accurate detection of certain relevant patient motion, such as symptoms of a movement disorder.

In one embodiment, IMD 14 may analyze the relative motion between activity sensors 16A and 16B. As described above, activity sensor 16A may be located on or within the housing of IMD 14 and activity sensor 16B may be located on or within a lead coupled to IMD 14. In the example illustrated in FIG. 1, the relative motion between activity sensor 16A and 16B represents the relative motion of the head of patient 12 relative to the torso of patient 12. Particular head movements relative to the torso may be indicative of an onset of a symptom of one or more movement disorders. In another embodiment, IMD 14 may analyze the relative motion between activity sensors 16A and 16C. In this case, IMD 14 analyzes the relative motion of the limb of patient 12 relative to the torso of patient 12. Again, particular limb movements relative to the torso may be indicative of an onset of a symptom of one or more movement disorders. As will be described in more detail below, IMD 14 may analyze the relative motion to detect one or more symptoms of the movement disorder. These techniques may be used to analyze the relative motion between any of activity sensors 16 and thus any locations of patient 12. In some embodiments, system 10 may include a monitoring device (not shown) that analyzes the relative motion between two or more of activity sensors 16 and sends a signal to IMD 14 to adjust the therapy upon detecting abnormal movements of patient 12.

IMD 14 may adjust the therapy delivered to patient 12 based on the relative motion between activity sensors 16. For example, IMD 14 may adjust one or more therapy parameters, such as stimulation amplitude, pulse width, pulse rate, electrode configuration, or other therapy parameters based on the relative motion detected between activity sensors 16. Adjustments to the therapy delivered to patient 12 may be made substantially in real-time as the relative motion between activity sensors 16 changes. Furthermore, adjusting the therapy delivered to patient 12 may, in some embodiments, include initiating or terminating delivery of therapy to patient 12. Accordingly, in some embodiments, IMD 14 may deliver therapy that is responsive to symptomatic movement detected via sensors 16.

System 10 may also include a clinician programmer 18 and a patient programmer 19. Clinician programmer 18 may be a handheld computing device that permits a clinician to program the therapy for patient 12, e.g., using input keys and a display. The clinician may use clinician programmer 18 to communicate with IMD 14 both during initial programming of IMD 14, and for collection of information and further programming during follow-up visits. For example, using clinician programmer 18, the clinician may specify therapy parameters for use in delivery of neurostimulation therapy. Additionally, the clinician can also retrieve operational or physiological data stored by IMD 14. In this manner, the clinician may periodically interrogate IMD 14 to evaluate efficacy and, if necessary, modify the stimulation parameters.

Like clinician programmer 18, patient programmer 19 may be a handheld computing device. Patient programmer 19 may also include a display and input keys to allow patient 12 to interact with patient programmer 19 and IMD 14. In this manner, patient programmer 19 provides patient 12 with an interface for control of the therapy delivered by IMD 14. For example, patient 12 may use patient programmer 19 to start, stop or adjust the therapy. In particular, patient programmer 19 may permit patient 12 to adjust therapy parameters such as duration, amplitude, pulse width and pulse rate, within an adjustment range specified by the clinician via clinician programmer 18, or select from a library of stored stimulation therapy programs.

IMD 14, clinician programmer 18, and patient programmer 19 may communicate via a wired or a wireless communication, as shown in FIG. 1. Clinician programmer 18 and patient programmer 19 may, for example, communicate via wireless communication with IMD 14 using RF telemetry techniques known in the art. Clinician programmer 18 and patient programmer 19 may also communicate with each other using any of a variety of local wireless communication techniques, such as RF communication according to the 802.11 or Bluetooth specification sets, infrared communication, e.g., according to the IrDA standard, or other standard or proprietary telemetry protocols.

Clinician programmer 18 and patient programmer 19 need not communicate wirelessly, however. For example, programmers 18 and 19 may communicate via a wired connection, such as via a serial communication cable, or via exchange of removable media, such as magnetic or optical disks, or memory cards or sticks. Further, clinician programmer 18 may communicate with one or both of IMD 14 and patient programmer 19 via remote telemetry techniques known in the art, communicating via a local area network (LAN), wide area network (WAN), public switched telephone network (PSTN), or cellular telephone network, for example.

Clinician and patient programmers 18, 19 are not limited to the hand-held computer embodiments illustrated in FIG. 1A. Programmers 18, 19 according to the invention may be any sort of computing device. For example, a programmer 18, 19 according to the invention may be a tablet-based computing device, a desktop computing device, or a workstation.

The techniques described herein are not limited to implementation via an IMD that delivers brain stimulation. For example, in some embodiments, the techniques may be used by an implantable device implanted elsewhere in patient 12 or for other purposes, e.g., an IMD implanted to provide spinal cord stimulation (SCS). As further examples, one or more leads 16 may be implanted proximate to the pelvic nerves (not shown) or stomach (not shown), and an IMD may deliver therapy to treat incontinence or gastroparesis. Additionally, leads 16 may be implanted on or within the heart to treat any of a variety of cardiac disorders, such as congestive heart failure or arrhythmia, or may be implanted proximate to any peripheral nerves to treat any of a variety of disorders, such as peripheral neuropathy or other types of chronic pain.

Although described herein with reference to embodiments in which IMD 14 adjusts therapy based on relative motion between sensors 16, the invention is not so limited. For example, in other embodiments, one or both of programmers 18, 19 may employ any of the techniques described herein to adjust therapy based on relative motion between sensors 16. The programmers may receive values from the sensors directly via wireless communication, or via wireless communication with IMD 14. The programmers may implement therapy changes through wireless communication with IMD 14.

Figure 2:
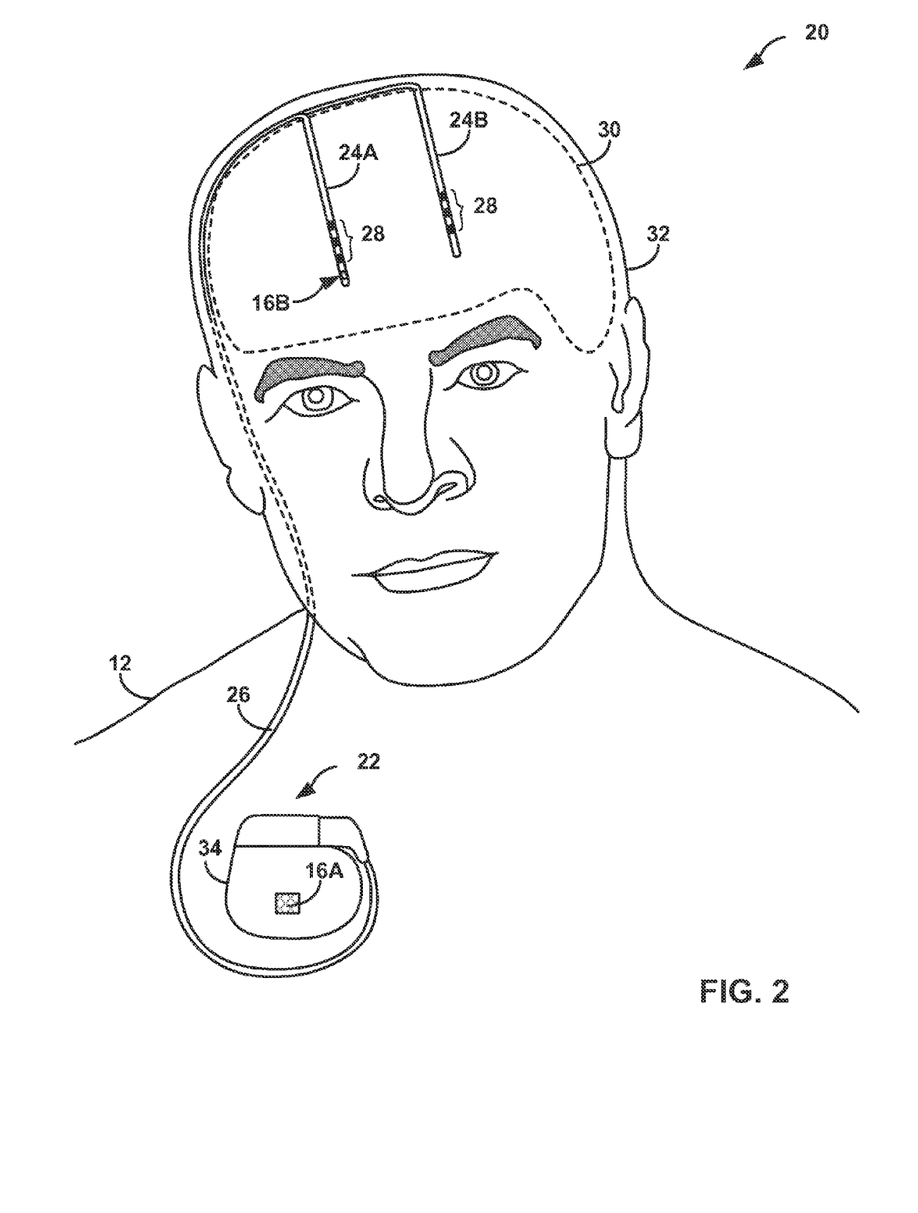
FIG. 2 is a conceptual diagram illustrating an example neurostimulator for providing brain stimulation.

FIG. 2 is a conceptual diagram illustrating an example therapy delivery system 20. Therapy delivery system 20 includes an implantable neurostimulator 22, which may be substantially similar to IMD 14 discussed above with reference to FIG. 1, that controls delivery of a therapy to patient 12 based on a relative motion between two or more activity sensors. Neurostimulator 22 may be able to adjust the therapy to treat and/or reduce the severity of one or more symptoms of any of a variety of movement disorders.

Neurostimulator 22 delivers neurostimulation therapy in the form of electrical pulses to patient 12. In particular, neurostimulator 22 delivers neurostimulation therapy to patient 12 via leads 24A and 24B (collectively, "leads 24"). Each of leads 24 include a lead body that extends from a proximal end that is coupled to neurostimulator 22 and to a distal end proximal to a target therapy delivery site. The proximal end of leads 24 may electrically and mechanically coupled to neurostimulator 22 either directly or indirectly, e.g., via a lead extension 26. Each of leads 24 includes one or more electrodes 28 that deliver the electrical pulses to the target therapy delivery site. One or more conductors may be disposed in lead body 26 and electrically connect electrodes 28 to neurostimulator 22. Electrodes 28 may, for example, be ring electrodes.

In the example shown in FIG. 2, leads 24 may extend to brain 30 of patient 12, e.g., through cranium 32 of patient 12. Neurostimulator 22 may deliver deep brain stimulation (DBS) or cortical stimulation therapy to patient 12 via electrodes 28 of leads 24 to treat any of a variety of movement disorders, including tremor, Parkinson's disease, spasticity, epilepsy or dystonia. However, the invention is not limited to the configuration of leads 24 and electrodes 28 shown in FIG. 2, or to the delivery of DBS therapy. For example, in another embodiment, one or more leads 24 may be implanted proximate to a spinal cord of patient 12, and neurostimulator 22 may deliver spinal cord stimulation (SCS) therapy to patient 12 via electrodes 28 to reduce pain experienced by patient 12. As further examples, one or more leads 24 may be implanted proximate to the pelvic nerves or a stomach of patient 12, and neurostimulator 22 may deliver neurostimulation therapy via electrodes 28 to treat incontinence or gastroparesis. Additionally, leads 24 may be implanted on or within the heart to treat any of a variety of cardiac disorders, such as congestive heart failure or arrhythmia, or may be implanted proximate to any peripheral nerves to treat any of a variety of disorders, such as peripheral neuropathy or other types of chronic pain. Moreover, the illustrated numbers and locations of leads 16 and electrodes 24 are merely examples. Embodiments of this disclosure may be utilized with any number of leads 24 implanted at any of a variety of locations within patient 12 with any number and configuration of electrodes 28.

As mentioned above, therapy delivery system 20 includes two or more activity sensors. In the embodiment illustrated in FIG. 2, therapy delivery system 20 includes activity sensors 16A and 16B that detect activity or motion of patient 12. Again, activity sensors 16 may comprise accelerometers that detect motions of patient 12. Activity sensor 16A is located on or within a housing 34 of neurostimulator 22. Activity sensor 16B is located on or within lead 24A. In particular, activity sensor 16B is located at the distal end of lead 24A proximal to the target delivery site. Although not shown in FIG. 2, lead 24B may also include an activity sensor on or within the lead.

Activity sensors 16 detect activity or motion at respective locations of patient 12. As patient 12 moves, activity sensor 16A detects the motion of the torso of patient 12 based on the motion of neurostimulator 22. Likewise, activity sensor 16B detects the motion of the head of patient 12 based on the motion of lead 24A implanted within the brain of patient 12. In the case in which activity sensors 16 comprise multi-axis accelerometers, the accelerometers detect the motion of the head and torso in terms of magnitude and direction. Activity sensors 16 may generate signals as a function of the detected motion.

Neurostimulator 22 receives the signals of activity sensors 16 and compares the signals from of activity sensors 16A and 16B to determine a relative motion between activity sensors 16A and 16B. In this case, the relative motion represents the motion of the head relative to the motion of the torso of patient 12. As described above, however, neurostimulator 22 may receive signals from activity sensors located elsewhere on patient 12, such as activity sensor 16C (FIG. 1) that is located on a limb of patient 12. In this case, neurostimulator 22 may determine a relative motion between activity sensor 16C (FIG. 1) and either activity sensor 16A or activity sensor 16B.

As mentioned above, neurostimulator 22 may analyze the relative motion between the activity sensors to detect patterns of movement that may be indicative of an onset of a symptom of a disorder e.g., a movement disorder. Alternatively, a monitoring device may generate and analyze the relative motion and send a signal to neurostimulator 22 upon detecting abnormal movement indicative of a symptom of the movement disorder. Neurostimulator 22 may adjust the therapy delivered to patient 12 based on the relative motion between activity sensors 16. For example, neurostimulator 22 may adjust one or more therapy parameters, such as stimulation amplitude, pulse width, pulse rate, electrode configuration or other therapy parameters upon determining that the relative motion detected between activity sensors 16 is indicative of a symptom of the disorder. Adjustments to the therapy delivered to patient 12 may be made substantially in real-time as the relative motion between activity sensors 16 changes, and may include initiating or terminating delivery of a therapy.

Figure 3:
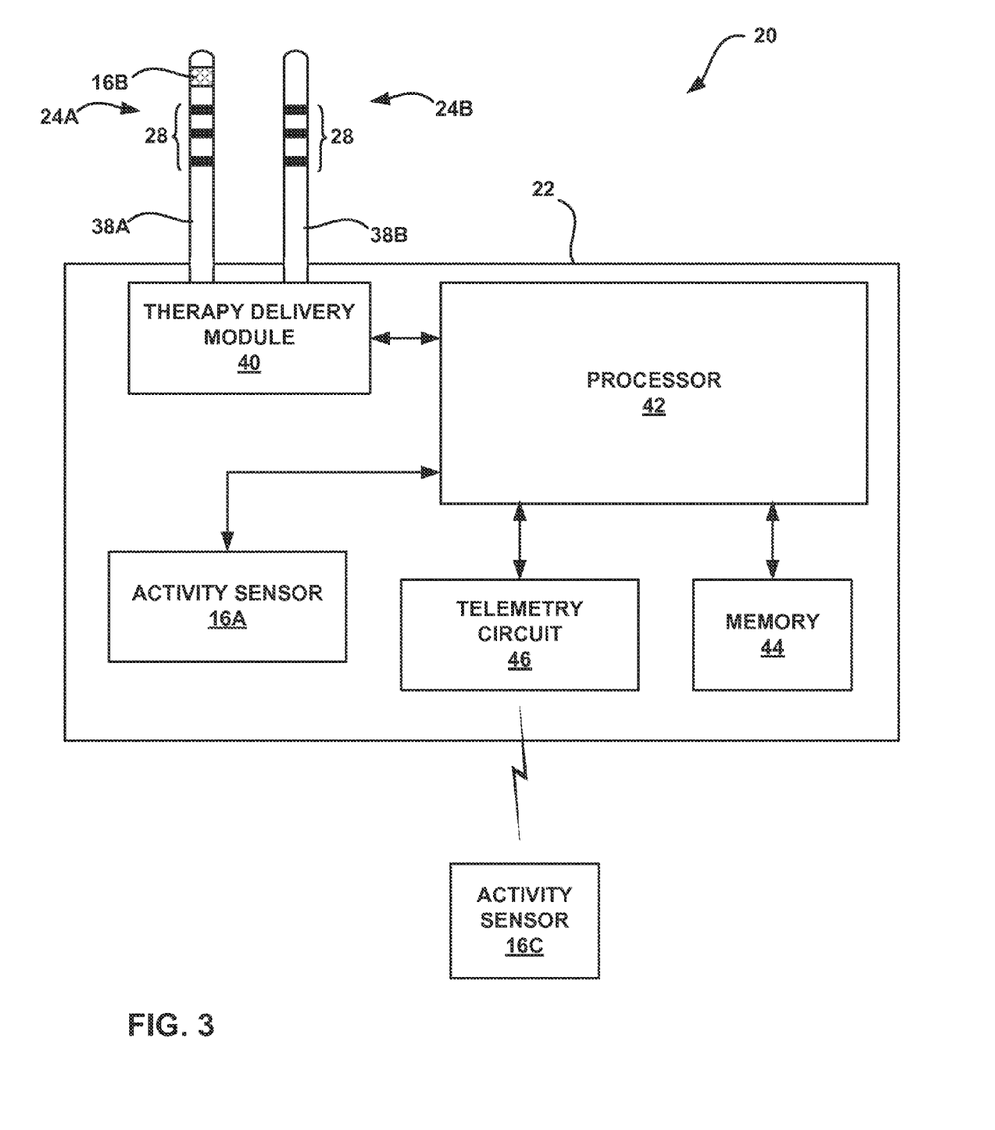
FIG. 3 is a block diagram illustrating various components of the neurostimulator of FIG. 2 in further detail.

FIG. 3 is a block diagram illustrating various components of therapy delivery system 20. Neurostimulator 22 delivers neurostimulation therapy via electrodes 28 of leads 24A and 24B (collectively, "leads 24"). Lead 24A includes an elongated lead body 38A and lead 24B includes an elongated lead body 38B. As described above, lead body 38A and 38B extend between a proximal end that couples to neurostimulator 22 and a distal end located proximate to the target stimulation delivery site. Lead body 38A and 38B may be a cylindrical or may be a paddle-shaped (i.e., a "paddle" lead). In the example illustrated in FIG. 3, electrodes 28 are disposed on a respective lead body 38 adjacent to the distal end of lead body 38, i.e., proximate to the target stimulation delivery site. In some embodiments, electrodes 40 may be ring electrodes. In other embodiments, electrodes 28 may be segmented or partial ring electrodes, each of which extends along an arc less than 360 degrees (e.g., 90-120 degrees) around the periphery of lead body 38. In embodiments in which lead 14 is a paddle lead, electrodes 28 may be pad electrodes located on one side of lead body 38. Electrodes 28 extending around a portion of the circumference of lead body 38 or located on one side of a paddle lead may be useful for providing an electrical stimulation field in a particular direction/targeting a particular therapy delivery site. The configuration, type, and number of electrodes 28 illustrated in FIG. 3 are merely an example.

Lead 24A also includes an activity sensor 16B coupled to lead body 38A. In the illustrated embodiment, activity sensor 16B is located proximate to the distal end of lead body 38A and distal to electrodes 28. In other embodiments, activity sensor 16B may be positioned between two of electrodes 28 or proximal on lead 24A relative to electrodes 28. Activity sensor 16B may be coupled to an outer surface of lead body 38A or located within lead body 38A. As described above, activity sensor 16B detects motion of the distal end of lead 24A and, more specifically, the motion of the portion of patient in which lead 24A is implanted, e.g., a head in the case of DBS therapy. Although not illustrated in FIG. 3, lead body 24B may also include an activity sensor on or within lead body 28B. Thus, system 20 may include an activity sensor on a single lead, or in some embodiments, activity sensors on multiple leads.

Electrodes 28 are electrically coupled to a therapy delivery module 40 via leads 24. In one embodiment, a pulse generator or other signal generation circuitry within therapy delivery module 40 delivers electrical signals (e.g., pulses or substantially continuous-time signals, such as sinusoidal signals) to target stimulation site via at least some of electrodes 28 under the control of a processor 42. Therapy delivery module 40 may, for example, include an electrical pulse generator coupled to a power source such as a battery (not shown in FIG. 3). Processor 42 controls therapy delivery module 40 to deliver neurostimulation therapy according to one or more neurostimulation therapy parameter sets, e.g., programs, selected from available parameter sets stored in a memory 44.

Processor 42 may include one or more microprocessors, controllers, digital signal processor (DSPs), application specific integrated circuits (ASICs), field-programmable gate arrays (FPGAs), discrete logic circuitry or the like. Memory 44 may include any volatile, non-volatile, magnetic, optical, or electrical media, such as a random access memory (RAM), read-only memory (ROM), non-volatile RAM (NVRAM), electrically-erasable programmable ROM (EEPROM), flash memory and the like. In some embodiments, memory 44 stores program instructions that, when executed by processor 42, cause neurostimulator 22 and processor 42 to perform the functions attributed to them herein.

Neurostimulator 22 may also include a telemetry circuit 46 that enables processor 42 to communicate with clinician programmer 18 (FIG. 1) and patient programmer 19 (FIG. 1). Via telemetry circuit 46, processor 42 may receive therapy parameter sets specified by a clinician from clinician programmer 18 for storage in memory 44. Processor 42 may also receive therapy parameter set selections and therapy adjustments made by patient 12 using patient programmer 19 via telemetry circuit 46. In some embodiments, processor 42 may provide diagnostic information recorded by processor 42 and stored in memory 44 to one of programmers 18, 19 via telemetry circuit 46. Telemetry circuit 46 also enables processor 42 to communicate with one or more activity sensors, such as activity sensor 16C. Processor 42 may, for example, receive signals that represent the detected motion from activity sensor 16C, which may be located on a limb of patient 12. As described above, activity sensor 16C senses the movement of the limb to which it is attached.

Processor 42 also interfaces with activity sensor 16A. Activity sensor 16A may be coupled to the housing of neurostimulator 22, or located within the housing of neurostimulator 22. In either case, activity sensor 16A senses the movement of neurostimulator 22. The signals sensed via activity sensor 16A as well as those sensed via activity sensor 16B and activity sensor 16C may be sent to processor 42 for analysis. As described above, the detected motion of activity sensors 16 represent the motion of the locations at which the activity sensors 16 are located.

Processor 42 may compare two or more of the signals received from activity sensors 16 to determine the relative motion between the locations of patient 12. In one embodiment, for example, processor 42 may calculate the difference between the signals generated by activity sensor 16A and activity sensor 16C. In other words, processor 42 computes the relative motion of activity sensor 16C relative to activity sensor 16A, and thus the relative motion of the limb of patient 12 to which activity sensor 16C is attached relative to the torso of patient 12. In another embodiment, processor 42 may calculate the difference between the signals generated by activity sensor 16A and activity sensor 16B. In this case, processor 42 computes the relative motion of activity sensor 16B relative to activity sensor 16A, and thus the relative motion of the head of patient 12 relative to the torso of patient 12. In a further embodiment, processor 42 may calculate the difference between the signals generated by activity sensor 16B and activity sensor 16C. In other words, processor 42 computes the relative motion of activity sensor 16C relative to activity sensor 16B, and thus the relative motion of the limb of patient 12 relative to the head of patient 12. These calculations may be performed substantially in real-time.

Using relative motion provides a different frame of reference. More specifically, instead of the frame of reference being no motion (i.e., stillness), the frame of reference is another activity sensor. This new frame of reference from the perspective of another one of activity sensors 16 allows the neurostimulator to ignore motions that are experienced by all portions of the body, thus making it easier to detect, for example, motions that represent conditions of movement disorder. In other words, using the new frame of reference provided by analyzing the relative motion between two or more activity sensors 16, the neurostimulator may ignore motion that is experienced by both the activity sensors 16. In the example of the bumpy plane ride above, both of the activity sensors experience the motion due to the turbulence. When compared to one another (e.g., subtracted) these detected motions may be substantially eliminated, leaving only the motions of the sensors that are different, such as the motions caused by a tremor or a seizure. In this manner, the new frame of reference provided by analyzing relative motion allows for more accurate detection of such conditions of movement disorders.

Processor 42 may compare the magnitudes of the signals generated by the two or more activity sensors, the directionality of the signals generated by the two or more activity sensors, the frequency of signals generated by two or more activity sensors or a combination thereof to calculate the relative motion. Processor 42 may then analyze the relative motion to detect a condition of a movement disorder. For example, processor 42 may analyze a plurality of relative motion measurements computed over a window of time, e.g., over 15-20 relative motion measurements. Processor 42 may detect a condition, such as a tremor or seizure, of a movement disorder when the magnitude, frequency and/or the directionality of the relative motion measurements exceed a threshold for a consecutive number of measurements. For instance, processor 42 may detect a condition of the movement disorder when relative motion is detected between the two sensors for a threshold number of times over a time period.

Alternatively, processor 42 may compare the relative motion over a window of time to one or more pre-defined patterns, and detect a condition of a movement disorder when the relative motion measurements over the window of time substantially match one of the pre-defined patterns. Processor 42 may determine the pre-defined patterns based on relative motion measurements computed during previous episodes, e.g., previous tremors or seizures, of patient. Pre-defined patterns may also be determined based on sensor signals obtained from a population of patients and/or clinical subjects during symptomatic movement episodes, e.g., tremors or seizures. In some embodiments, processor 42 may employ or include a neural network for the purpose of identifying symptomatic movement. The neural network may be trained based on prior patient episodes and/or episodes gathered from other patients/subjects.

Alternatively, processor 42 may compute the pre-defined patterns based on a basic body model. The body model may, for example, represent information regarding patient 12 (e.g., height, weight and age), the position of activity sensors 16 within patient 12, or the like. Processor 42 may, for example, receive the body model information from a physician or patient via one of programmers 18, 19, e.g., during initial configuration of the device. Alternatively, programmers 18, 19 may compute look-up tables based on the body model. Processor 42 may use the body model information or other information generated from the body model to compute relative motions between two or more activity sensors 16 or to analyze the relative motion to identify abnormal movement. For example, processor 42 may use a variety of algorithms based on kinesiology and the biomechanics of the human body to predict relative motion measurements that are indicative of a condition of a movement disorder for the particular patient. Such computations may account for other variables such as age, weight and height of patient.

As described above, a separate device, such as a monitoring device may receive the signal generated by activity sensors 16 and compare the signals to compute the relative motion between the sensors. Additionally, the monitoring device may analyze the relative motion using the techniques described above to determine whether the relative motion is indicative of a symptom of the movement disorder. In another embodiment, neurostimulator 22 may include more than one processor, and one processor may analyze the relative motion and provide a signal to a second processor that controls the therapy when abnormal movement is detected.

In any case, processor 42 may control therapy delivery module 40 to deliver therapy to patient 12 based on the relative motion between two or more of activity sensors 16. As will be described in further detail below, processor 42 may change one or more therapy parameters to attempt to provide therapy to patient 12 that is more efficacious and/or better addresses the symptomatic movement indicated by the relative motion. For example, processor 42 may adjust electrode combinations used to deliver the therapy, electrode polarities of the selected electrodes, a stimulation amplitude, pulse width, pulse rate, or other therapy parameters based on the relative motion detected between the two or more activity sensors. Adjustments to the therapy delivered to patient 12 may be made substantially in real-time as patient experiences these symptoms, and may include initiating and terminating therapy.

Figure 4:
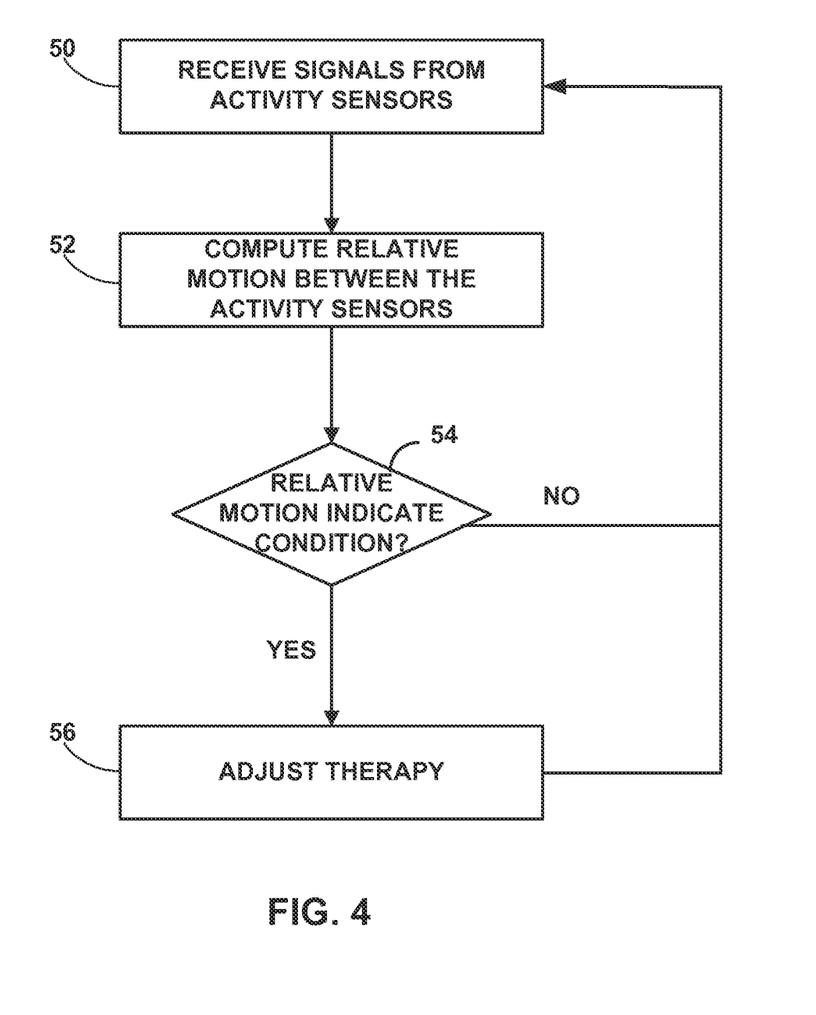
FIG. 4 is a flow diagram illustrating example operation of a therapy delivery device controlling therapy based on relative motion between two or more activity sensors.

FIG. 4 is a flowchart illustrating an example operation of a therapy delivery device, such as neurostimulator 22 of FIGS. 2 and 3, controlling therapy based on relative motion between two or more activity sensors. Initially, neurostimulator 22 receives signals from two or more activity sensors 16 (50). As described above, the signals are generated as a function of the motion detected by activity sensors 16. Neurostimulator 22 may receive the signals from activity sensors 16 via a wired connection, a wireless connection or a combination thereof. Alternatively, one or more of activity sensors 16 may transmit the signals to a separate monitoring device, which relays the signals to neurostimulator 22.

Processor 42 of neurostimulator 22 computes a relative motion between the activity sensors (52). As described above, processor 42 may, for example, calculate the difference between the signal generated by a first one of activity sensors 16 and a signal generated by a second one of activity sensors 16 to compute the relative motion between activity sensors 16. As described above, the relative motion between activity sensors 16 is representative of the relative motion between the locations of patient 12 at which the respective activity sensors 16 are located. As described in detail above, the relative motion provides a new reference frame from which to analyze the motion measurements. In particular, the relative motion provides a reference frame in which motion experienced by both activity sensors 16, e.g., motion caused the environment in which patient 12 is located, is removed. This leaves processor 42 with more pertinent information to make a determination regarding a condition of the movement disorder.

Processor 42 determines whether the computed relative motion is indicative of a condition of the movement disorder of patient 12 (54). As described above, processor may analyze magnitudes of one or more computed relative motions, the directionality of one or more computed relative motions, or both to make such a determination. Processor 42 adjusts the therapy delivered to patient 12 based on the relative motion (56). As discussed above, adjustment may include initiating responsive therapy, or terminating therapy, in some embodiments. For example, symptomatic motion detected based on relative motion between sensors 16 may be a side effect of therapy, in which case processor 42 may respond by reducing an amplitude or dosage of the therapy, or suspending or terminating the therapy.

Various embodiments have been described. These and other embodiments are within the scope of the following claims.

What is claimed is:

1. A system comprising:
a therapy delivery device configured to deliver a therapy to a patient;
a first activity sensor configured to generate a first signal as a function of motion at a torso of the patient;
a second activity sensor configured to generate a second signal as a function of motion at a location of a body of the patient, wherein the location is different from the torso of the patient; and
at least one processor configured to:
compare the first signal generated by the first activity sensor and the second signal generated by the second activity sensor to determine a relative motion of the location of the body of the patient relative to the torso; and
control, based on the relative motion, the therapy delivered to the patient.

2. The system of claim 1, wherein the first activity sensor is configured to be located on or within the torso of the patient, and wherein the second activity sensor is configured to be located on or within a head of the patient.

3. The system of claim 1, wherein the first activity sensor is configured to be located on or within the torso of the patient, and wherein the second activity sensor is configured to be located on or within a leg of the patient.

4. The system of claim 1, wherein the first activity sensor is configured to be located on or within the torso of the patient, and wherein the second activity sensor is configured to be located on or within an arm of the patient.

5. The system of claim 1, wherein the therapy delivery device comprises a housing, and wherein one of the first activity sensor or second activity sensor is located within the housing.

6. The system of claim 1, further comprising a lead coupled to the therapy delivery device and configured to deliver the therapy from the therapy delivery device to a target therapy delivery site of the patient, wherein one of the first activity sensor or the second activity sensor is coupled to the lead.

7. The system of claim 1, wherein at least one of the first activity sensor and the second activity sensor comprises transmit circuitry to wirelessly transmit, via wireless telemetry, the respective signal to the therapy delivery device.

8. The system of claim 1, wherein the therapy comprises spinal cord stimulation therapy.

9. The system of claim 1, wherein the at least one processor is configured to compare a difference in magnitude of the motions detected by the first activity sensor and the second activity sensor to determine a magnitude of the relative motion.

10. The system of claim 1, wherein the at least one processor is configured to compare a difference in directionality of the motions detected by the first activity sensor and the second activity sensor to determine a directionality of the relative motion.

11. The system of claim 1, wherein the at least one processor is configured to:
determine that the relative motion exceeds a threshold; and
control, based on the determination, the therapy delivered to the patient.

12. The system of claim 1, wherein the at least one processor is configured to adjust, based on the relative motion, at least one of an amplitude, a pulse width, a pulse rate, an electrode configuration, and a duration of the therapy delivered to the patient.

13. The system of claim 1, wherein the at least one processor is configured to control, based on the relative motion, the therapy delivered to the patient by one of initiating or terminating delivery of the therapy to the patient.

14. The system of claim 1, wherein the therapy delivery device comprises the at least one processor.

15. A method comprising:
  generating, by a first activity sensor, a first signal as a function of motion at a torso of a patient;
  generating, by a second activity sensor, a second signal as a function of motion at a location of the body of the patient, wherein the location is different from the torso of the patient;
  comparing, by one or more processors, the first signal generated by the first activity sensor and the second signal generated by the second activity sensor to determine a relative motion of the location of the body of the patient relative to the torso; and
  controlling, by the one or more processors and based on the relative motion, delivery of a therapy to the patient.

16. The method of claim 15, wherein the first activity sensor is configured to be located on or within the torso of the patient, and wherein the second activity sensor is configured to be located on or within a head of the patient.

17. The method of claim 15, wherein the first activity sensor is configured to be located on or within the torso of the patient, and wherein the second activity sensor is configured to be located on or within a leg of the patient.

18. The method of claim 15, wherein the first activity sensor is configured to be located on or within the torso of the patient, and wherein the second activity sensor is configured to be located on or within an arm of the patient.

19. The method of claim 15, further comprising wirelessly transmitting at least one of the first signal from the first activity sensor and the second signal from the second activity sensor to a therapy delivery device configured to deliver the therapy to the patient.

20. The method of claim 15, wherein the therapy comprises spinal cord stimulation therapy.

21. The method of claim 15, further comprising comparing a difference in magnitude of the motions detected by the first activity sensor and the second activity sensor to determine a magnitude of the relative motion.

22. The method of claim 15, further comprising comparing a difference in directionality of the motions detected by the first activity sensor and the second activity sensor to determine a directionality of the relative motion.

23. The method of claim 15, further comprising determining that the relative motion exceeds a threshold, wherein controlling delivery of the therapy comprises controlling, based on the determination, the therapy delivered to the patient.

24. A system comprising:
  means for generating a first signal as a function of motion at a torso of a patient;
  means for generating a second signal as a function of motion at a location of the body of the patient, wherein the location is different from the torso of the patient;
  means for comparing the first signal and the second signal to determine a relative motion of the location of the body of the patient relative to the torso; and
  means for controlling, based on the relative motion, delivery of a therapy to the patient.

* * * * *